United States Patent [19]
Engberg et al.

[11] Patent Number: 5,732,181
[45] Date of Patent: Mar. 24, 1998

[54] FANOUT DEVICE FOR OPTICAL FIBERS OF A MULTI-FIBER CABLE

[75] Inventors: Kristian R. Engberg, Sollentuna; Anders N. Sjöberg, Bromma, both of Sweden

[73] Assignee: Telefonaktiebolaget LM Ericsson, Stockholm, Sweden

[21] Appl. No.: 719,975

[22] Filed: Sep. 24, 1996

[30] Foreign Application Priority Data

Sep. 10, 1995 [SE] Sweden ................... 9503499

[51] Int. Cl.⁶ ........................................ G02B 6/00
[52] U.S. Cl. ...................... 385/139; 385/24; 385/31; 385/45; 385/49; 385/50
[58] Field of Search ....................... 385/139, 14, 22, 385/24, 31, 39–50

[56] References Cited

U.S. PATENT DOCUMENTS 5,343,544  8/1994  Boyd et al. ................ 385/45 X

FOREIGN PATENT DOCUMENTS

| 61-121012 | 6/1986 | Japan . |
| A 2-67503 | 3/1990 | Japan . |
| 176077 | 10/1994 | Norway . |

OTHER PUBLICATIONS

Patent Abstracts of Japan, vol. 14, No. 253, P–1054, abstract of JP, A, 2–67503 (Nippon Electric Glass Co. Ltd.), 7 Mar. 1990 (Mar. 7, 1990).

Primary Examiner—Phan T. H. Palmer
Attorney, Agent, or Firm—Burns, Doane, Swecker & Mathis, L.L.P.

[57] ABSTRACT

The present invention relates to a fanout device for separating and encapsulating glass fibers of a multi-fiber cable. The invention also relates to a method of manufacturing a fanout device. A multi-fiber cable from which part of the sheath (1, 21) has been removed is placed in a jig (5) with the glass fibers (3, 24) mutually separated in an optical coupling device and with one end of respective fibers encapsulated in a respective glass tube (8, 20). The inventive fanout is comprised of two plates (9, 10, 22, 23) provided on one side with an adhesive substance, and the adhesive side (14) of the first plate (9, 21) is pressed against the jig surface that contains the glass fibers (3, 24) in accordance with the above, so that these fibers fasten to the plates (9, 22). The first plate (9, 22) is then lifted from the fixture surface and the adhesive side (15) of the second plate (10, 23) is pressed against the adhesive side (14) of the first plate such as to enclose and encapsulate the glass fibers (3, 24) between the plates (9, 10, 22, 23). The thus encapsulated fanout is placed finally in a shockproof box (12) having a snap-on lid (11).

11 Claims, 3 Drawing Sheets

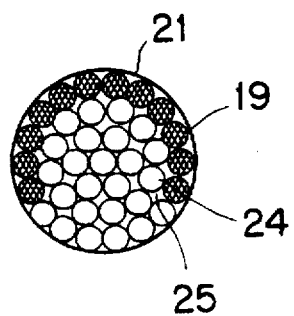
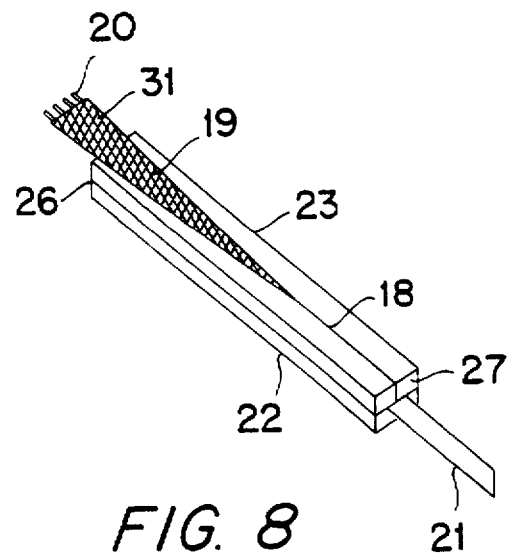
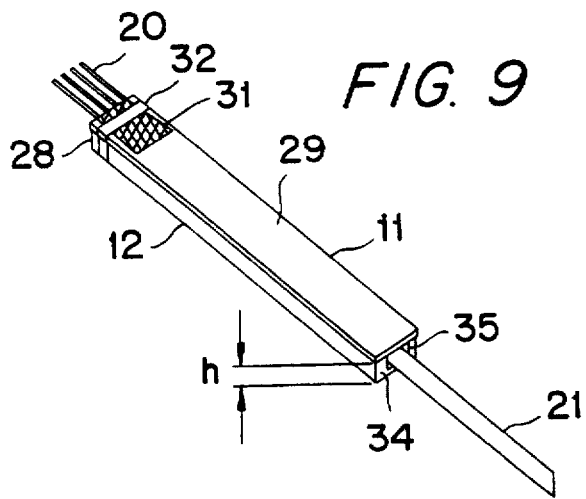

FANOUT DEVICE FOR OPTICAL FIBERS OF A MULTI-FIBER CABLE

FIELD OF INVENTION

The present invention relates to a fanout device for separating and encapsulating the individual fibers in a multi-fiber cable in a controlled manner.

DESCRIPTION OF THE BACKGROUND ART

The function of a fanout is to separate the individual optical fibers of a multi-fiber cable in a manner such that the fibers will not be twisted, bent or impart optical damping to the transmission link in any other way. A fanout can be used in those instances when it is necessary to divide multi-fiber cables into separate fibers, as in optical coupling devices and in cross-connection units.

According to known techniques, a fanout is a jig which functions to hold the glass fibers of a multi-fiber cable separated from one another. The jig includes a partially penetrating front recess on a first jig surface, this surface extending from the centre of one short side of the jig and slightly in towards the centre thereof, and several non-penetrating narrow rear recesses on the first surface of the jig that extend from the centre of the opposite short side of the jig and slightly in towards the centre thereof, and V-grooves on said first jig surface that connect the front recess with the rear recesses. A plurality of fibers that have been exposed by removing part of the cable sheath are placed in an optical coupling box and protected by protective tubes placed on their outer ends, whereafter the multi-fiber cable is placed in the front recess of the jig and the mutually separated glass fibers are placed in respective V-grooves in said jig and the protective tubes are placed in respective rear recesses on the jig. The known fanout has the disadvantage of being expensive and the work involved in placing the fibers in the jig takes a relatively long time to complete.

Japanese Patent Publication JP 2-67503 discloses a device for affixing glass tubes containing optical fibers on a base plate. The glass tubes are placed in V-grooves in a jig and an adhesive-coated base plate is pressed onto the glass tubes. The base plate is illuminated with light to harden the adhesive, whereafter the base plate and the glass tubes affixed thereto are removed from the jig. The device can therewith be manufactured more cheaply, and the loss entailed by installation of the optical fibers is also reduced.

The Japanese Patent Publication JP 61-121012 describes the short time manufacture of optical circuit parts with high precision, by using a jig and a substrate. Optical elements are placed in a given position in V-grooves provided in the jig at a desired angle of inclination. The substrate is pressed against the surface of the jig so that the optical elements fasten to said substrate, which is then removed from the jig.

Norwegian Patent Publication NO 924644 discloses a device for placing a plurality of coated optical fibers in a plane with a predetermined spacing therebetween. The coated optical fibers are placed in a slot in a device that includes a number of setting or adjusting means at one end of the slot for adjusting the spacing between the optical fibers disposed in the slot. The optical fibers are fixated by means of an adhesive tape placed transversely across the slot.

SUMMARY OF THE INVENTION

The object of the present invention is to provide a simple and inexpensive fanout device which functions to hold glass fibers in a slitted multi-fiber cable separated from one another, and which encapsulates said fibers.

The problem to which the present invention is directed is one of manufacturing an inexpensive fanout device which will enable glass fibers of a multi-fiber cable to be fixated and encapsulated in a simple and rational manner.

This object is achieved by pressing an adhesive coated side of a first plate against the surface of a jig which includes V-grooves in which there are placed glass fibers which have been mutually separated in an optical coupling box from a multi-fiber cable from which part of the sheath has been stripped and which have protective tubes placed on the ends thereof. The plate fixates the glass fibers, the protective tubes and the cable on its adhesive surface and is then removed from the surface of the jig. An adhesive coated side of a second plate is then pressed against the first adhesive side of the first plate, so as to encapsulate the glass fibers between the plates. The thus encapsulated fanout is then placed in shockproof box provided with a lid.

The inventive fanout device has the advantage of being inexpensive and easy to manufacture. Several inventive fanout devices can be produced from a single jig, such jigs being expensive to produce and difficult to use.

BRIEF DESCRIPTION OF THE DRAWINGS

The invention will now be described with reference to an exemplifying embodiment thereof and also with reference to the accompanying drawings, in which

FIG. 7 is a cross-sectional view of a multi-fiber cable comprising sheathed Kevlar fibers according to known techniques;

FIG. 8 is a perspective view of an alternative embodiment of the invention, wherein two pieces of adhesive tape include a plurality of mutually separated glass fibers in a multi-fiber cable, and wherein the upper piece of tape has in its rear end a slot through welch the Kevlar fibers can be drawn; and FIG. 9 is a perspective view of a tension load relieving device according to the alternative embodiment, wherein the tape capsule in FIG. 8 is placed in a box provided with a lid and the Kevlar fibers are fastened to the upper side of the lid with a piece of adhesive tape.

DESCRIPTION OF PREFERRED EMBODIMENTS

Figure 1:
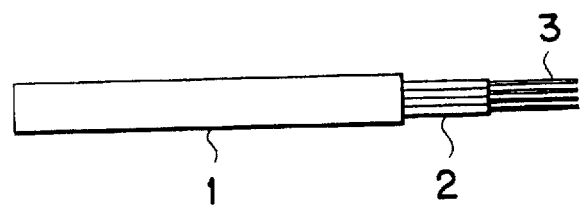
FIG. 1 illustrates schematically a known multi-fiber cable.

FIG. 1 illustrates schematically a multi-fiber cable which includes a plurality of glass fibers 3 that are covered with a primary protective 2 and which are held fixed in relation to one another by means of an outer protective sheath 1.

Figure 2:
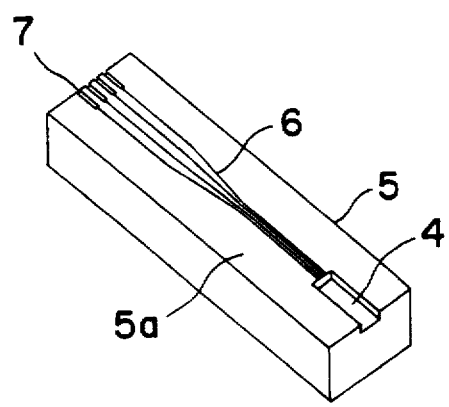
FIG. 2 illustrates from above a jig which is used to hold the glass fibers of a multi-fibers cable separated in accordance with a known technique.

In earlier known techniques, the fibers of a multi-fiber cable are separated in an optical coupling box. FIG. 2 illustrates a known fanout device for maintaining the glass fibers 3 of a multi-fiber cable separated from one another. The illustrated jig 5 includes a front recess 4 which accommodates the cable sheath 1, and several rear recesses 7 for accommodating the protective tubes 8, and V-grooves 6 which receive the glass fibers 3.

Figure 3:
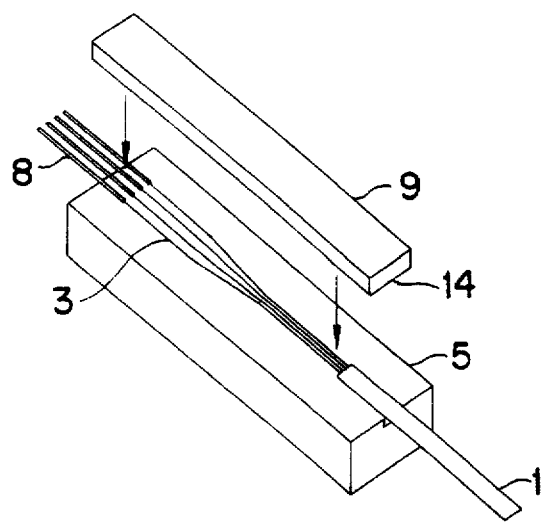
FIG. 3 is a perspective view of an inventive jig where a piece of adhesive tape is pressed against a jig to fixate a plurality of mutually separated glass fibers.
Figure 4:
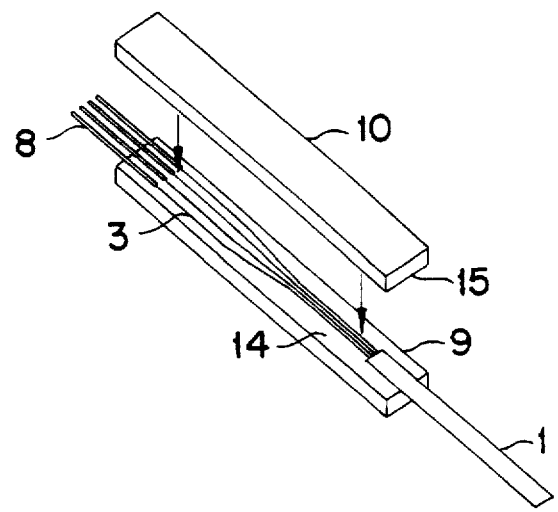
FIG. 4 is a perspective view of the inventive device in which two pieces of adhesive tape are fastened around plurality of mutually separated glass fibers.
Figure 5:
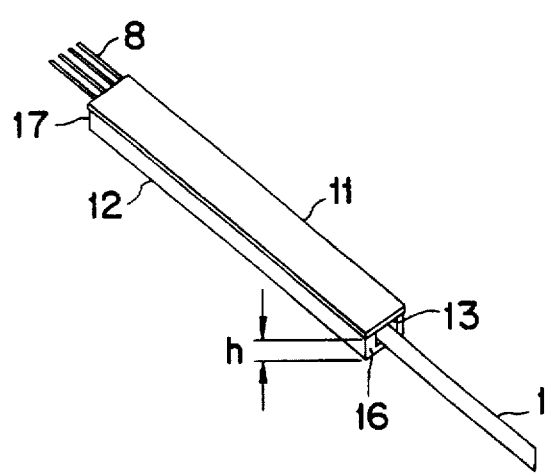
FIG. 5 is a perspective view of a shockproof box provided with a lid and containing the fanout encapsulated in accordance with the invention.

An exemplifying embodiment of the invention is illustrated in FIGS. 3–5. Fiber separation in the inventive fanout device is achieved with the aid of a jig 5. A given length of sheath 1 is removed from the outer end of a multi-fiber cable and the glass fibers 3 thus exposed are mutually separated in an optical coupling box and the outer ends of the fibers fitted with protective tubes 8. The cable is placed in the front recess 4 in the jig and the separated fibers 3 are placed in the V-grooves e and the glass tubes 8 are placed in the rear recesses 7 in the jig. A first piece of tape 9 coated with an adhesive on one side 14 and having a size suitable for the purpose intended is pressed onto that surface of the jig 5 which contains the glass fibers 3. The first piece of tape 9 is then removed from the jig 5 with the cable sheath 1, the protective tubes 8 and the glass fibers 3 firmly affixed to the adhesive side 14 of said first tape. An adhesive coated surface 15 of a second piece of tape 10 is then pressed onto the side 14 of the first tape piece. The tape pieces 9, 10 completely enclose the glass fibers together with a length of sheath 1 and a length of glass tubes 8. The thus encapsulated fanout is placed finally in an impact proof box 12.

The sides of the first and the second tape pieces 9 and 10 opposite to the adhesive coated sides 14, 15 are coated with foamed backing material to protect the glass fibers 3 from external moisture and dirt. The elastic property of the backing material will ensure that an efficient seal is obtained around the incoming and outgoing fibers 3 and also around the sheath 1. The impact proof box 12 may be made of a plastic material and have a sheath accommodating aperture 13 in one side 16 of the box and a protective tube accommodating aperture in a side 17 thereof, said box 12 being provided with a snap-on lid 11; see FIG. 5. The vertical extension h of the box 12 is smaller than the encapsulated fanout, so that the fanout will project outwardly from the box short sides 16, 17. The backing material on the first tape piece 9 and the second tape piece 10 will be compressed as the box 12 is closed, therewith improving the moisture and dirt seal and stabilizing the encapsulated fanout in the box 12 and prevent it from sliding around.

The tape pieces 9, 10 may be integrated with a supplementary carrier layer, e.g. a metal layer, so as to obtain a stiffer construction. Improved encapsulation and greater mechanical strength can be obtained by securing the sheath 1 in the box 12 with glue.

Thin flexible bands or flexible plates may be used as an alternative to the tape pieces 9, 10 of the afore described embodiment.

An alternative embodiment of the invention is shown in FIGS. 7"9. The glass fibers of a multi-fiber cable are sensitive and unable to withstand excessive external loads. The use of a multi-fiber cable that has Kevlar fibers 19 integrated within the sheath 21 will provide a stronger cable construction, since the largest part of an external load will be taken up by the Kevlar fibers 19. FIG. 7 is a cross-sectional view of a multi-fiber cable that includes Kevlar fibers. The glass fibers 24 are covered with a primary protective 25 and enclosed by a plurality of Kevlar fibers 19 which are held fixed in relation to one another by means of an outer protective layer, the cable sheath 21.

The glass fibers 24 of the cable are separated mutually in an optical coupling box and provided with protective tubes 20 on their outer ends and placed in a jig 5 in the same way as that described above. The adhesive surface of a first tape piece 22 is pressed onto the jig surface that contains the glass fibers 3, so that the sheath 21, the Kevlar fibers 19 and the glass fibers 24 fasten to the tape 22. The first tape piece 22 is then removed from the jig surface and the adhesive side of a second tape piece 23 is pressed onto the adhesive surface of the first tape piece 22, so that the tape pieces together enclose the glass fibers 24, the Kevlar fibers 19 and a part of the cable sheath 21. The rear part of the second tape piece 23 is provided along its long sides with a through penetrating slit 18 which extends from the midway point of the short side 27 of the second tape piece to the centre of said second tape piece 23, such as to enable the Kevlar fibers 19 within the cable sheath 21 to be moved upwards and forwards through the slit 18 and therewith separated from the glass fibers 24, such that the Kevlar fibers 19 will project slightly outwards of the short side 26 of the tape capsule. The thus encapsulated fanout is finally placed in a shockproof box 12 that has a cable accommodating aperture 35 in its short side 34 and an aperture for accommodating the protective tubes 20 and the Kevlar fibers 19 in its short side 28, said box 12 being provided with a snap-on lid 11, as evident from FIG. 9. The box 12 has a smaller vertical extension h than the encapsulated fanout, so that the fanout will project slightly above the short sides 28, 34 of the box. The Kevlar fibers 31 that project out from the box 12 are bent upwards and rearwards along the long side of the lid 11 and placed on the upper side 29 of the lid. The Kevlar fibers 31 are secured effectively to the lid 11 with the aid of adhesive tape 32 which is placed along the short side of the lid and down over the box 12, therewith ensuring that the encapsulated fanout will lie stably within the box 12.

Figure 6:
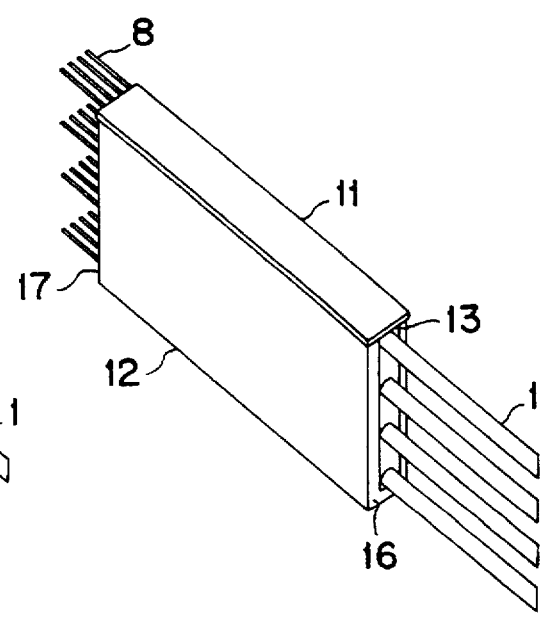
FIG. 6 is a perspective view of a plurality of mutually stacked capsulated fanouts housed in a shockproof box provided with a lid.

The advantage with the inventive fanout device is that it can be produced cheaply. Several encapsulated fanouts can be stacked in one and the same box 12 provided with lid 11, therewith saving space; see FIG. 6.

The fanout device provides a good seal against dirt and moisture from without, by virtue of the elastic, foamed backing material on the tape pieces. As the lid is closed, the backing material is compressed and therewith function to keep the fanout stable in the box and prevent the fanout from sliding in the box.

We claim:

1. A fanout device comprising:
    a first and second plate each having a surface, at least one of the surfaces being coated with an adhesive substance; and
    a plurality of mutually separated fibers of a partially unsheathed multi-fiber cable enclosed between the surfaces of the first and second plates, each of the fibers including an outer end encapsulated in a tube.

2. A fanout device according to claim 1, wherein the plates are located in a box having an aperture a sheath of the multi-fiber cable, and an aperture for receiving the protective tubes.

3. A fanout device according to claim 2 wherein the box includes several pairs of said plates stacked one upon the other.

4. A fanout device according to claim 2, wherein the lid of the box is a snap-on lid.

5. A fanout device according to claim 2, wherein the multi-fiber cable includes aromatic polyamide fibers integrated in a layer within the cable sheath, the second plate including a slit extending along a side of said second plate, the slit being sized to permit the aromatic polyamide fibers to pass through the slit wherein the aromatic polyamide fibers can project out from the box and can be fixed to the lid.

6. A fanout device according to claim 1, wherein a side of at least one of said plates located opposite of the surface of said plate is covered with a foamed backing material.

7. A fanout device according to claim 6, wherein the plates are located in a box having a lid, the box including an aperture for receiving a sheath of the multi-fiber cable and an aperture for receiving the protective tubes, and wherein a height of each of the two plates together is greater than a vertical extension of the box wherein when the lid is closed the foamed backing material on said plates is compressed.

8. A fanout device according to claim 1, wherein each of the surfaces of the first and second plates includes an adhesive.

9. A fanout device comprising:

an optical fiber assembly including a plurality of optical fibers each having a first portion located within a sheath, a second unsheathed portion and a third portion located within a tube, wherein said plurality of optical fibers are spaced further apart from one another along said second and third portions thereof than along said first portions to fanout said plurality of optical fibers;

a first and second piece secured to each other; said optical fiber assembly being located between said first and second pieces, said secured first and second pieces fixating said plurality of optical fibers in said fanned-out relationship.

10. A method of manufacturing a fanout device comprising the steps of:

removing a part of a sheath of a multi-fiber cable to expose fibers therein:

separating the fibers;

providing tubes on an outer end of each of the fibers;

placing the tubes, the sheath, and the fibers in a jig having:

a first surface with a sheath receiving recess, a plurality of tube accommodating recesses, and fiber receiving grooves connecting the sheath receiving recess with the tube accommodating recesses;

pressing a side of a first plate having an adhesive thereon against the first surface of the jig to fixate the fibers, the tubes and the sheath on the side of said plate;

removing the first plate from said first surface of the jig; and pressing a surface of a second plate against the side of the first plate so as to encapsulate and fixate the fibers between the first and second plates.

11. A method of manufacturing a fanout device comprising the steps of:

providing a jig having a plurality of spaced grooves;

placing a plurality of unsheathed optical fibers of an optical fiber cable in said spaced grooves of said jig to define a spaced relationship between said unsheathed optical fibers;

placing an adhesive surface of a first piece on said unsheathed optical fibers located in said grooves to adhere said unsheathed optical fibers to said adhesive surface in said spaced relationship; and securing a second piece to said first piece to fixate said optical fibers between said first and second pieces in said spaced relationship.

* * * * *